US011931493B2

(12) United States Patent
Nilsson et al.

(10) Patent No.: US 11,931,493 B2
(45) Date of Patent: Mar. 19, 2024

(54) PREPARING AN EXTRACORPOREAL BLOOD TREATMENT APPARATUS

(71) Applicant: Gambro Lundia AB, Lund (SE)

(72) Inventors: Roger Nilsson, Höör (SE); Björn Ericson, Lund (SE); Jonas Fors, Malmö (SE); Karl Henrik Forsland, Genarp (SE)

(73) Assignee: Gambro Lundia AB, Lund (SE)

( * ) Notice: Subject to any disclaimer, the term of this patent is extended or adjusted under 35 U.S.C. 154(b) by 386 days.

(21) Appl. No.: 17/293,228

(22) PCT Filed: Nov. 18, 2019

(86) PCT No.: PCT/EP2019/081567
§ 371 (c)(1),
(2) Date: May 12, 2021

(87) PCT Pub. No.: WO2020/109038
PCT Pub. Date: Jun. 4, 2020

(65) Prior Publication Data
US 2022/0047788 A1    Feb. 17, 2022

(30) Foreign Application Priority Data
Nov. 27, 2018 (SE) .................................. 1851466-1

(51) Int. Cl.
*A61M 1/16*    (2006.01)
(52) U.S. Cl.
CPC ........ *A61M 1/1601* (2014.02); *A61M 1/1668* (2014.02); *A61M 1/1688* (2014.02); *A61M 2205/50* (2013.01); *A61M 2205/7518* (2013.01)

(58) Field of Classification Search
CPC ... A61M 1/3647; A61M 1/3649; A61M 1/365
See application file for complete search history.

(56) References Cited

U.S. PATENT DOCUMENTS

| 2012/0204968 | A1  | 8/2012  | Fulkerson et al. |
| 2013/0112629 | A1* | 5/2013  | Brandl ............... A61M 1/1682 210/791 |
| 2020/0316283 | A1* | 10/2020 | Vecten ............ A61M 1/362265 |

FOREIGN PATENT DOCUMENTS

| EP | 1450879 B2  | 12/2015 |
| WO | 03006100 A1 | 1/2003  |

* cited by examiner

*Primary Examiner* — Benjamin M Kurtz
(74) *Attorney, Agent, or Firm* — K&L Gates LLP

(57) ABSTRACT

A control system is configured to implement a method of preparing a blood treatment apparatus (1) for blood treatment. The method comprises installing, by use of a disposable arrangement, first and second flow circuits (C1, C2) separated by a semi-permeable membrane (25), the first flow circuit (C1) being connected for fluid communication with the apparatus (1) and the second flow circuit (C2) being connected to form a closed loop that includes a sterilizing filter (46) and, optionally, a container (30). The method further comprises performing backfiltration to transfer a human-compatible fluid from the first flow circuit (C1) to the second flow circuit (C2) through the semi-permeable membrane (25), and circulating (304) the human-compatible fluid in the closed loop of second flow circuit (C2), to thereby sterilize the human-compatible fluid by the sterilizing filter (46) and, optionally, collect a resulting sterile fluid in the container (30) for later use.

18 Claims, 6 Drawing Sheets

PREPARING AN EXTRACORPOREAL BLOOD TREATMENT APPARATUS

PRIORITY CLAIM

The present application is a National Phase of International Application No. PCT/EP2019/081567, filed Nov. 18, 2019, which claims priority to Swedish Application No. 1851466-1, filed Nov. 27, 2018. The entire contents of each are incorporated herein by reference and relied upon.

TECHNICAL FIELD

The present invention relates to operating an extracorporeal blood treatment apparatus, e.g. a dialysis machine, and in particular to preparing such an apparatus for treatment.

BACKGROUND ART

Extracorporeal blood treatment, such as hemodialysis, is performed by an apparatus that is configured to supply one or more fluids for use in the treatment. Equipment that is exposed to blood during treatment is typically replaced after each treatment. Such disposable equipment may include a dialyzer and tubing for defining an extracorporeal circuit for conducting blood from a patient, through the dialyzer and back to the patient. Before connecting the patient to the extracorporeal circuit it is common practice to prime the extracorporeal circuit. The purpose of priming the circuit is to remove air from the blood lines and the dialyzer, to fill the blood lines and the dialyzer with a human-compatible liquid, as well as to remove possible fragments of remaining sterilizing agents or other residuals from the disposable equipment, before the patient is connected.

Conventionally, priming is performed by flowing a sterile saline solution through the extracorporeal circuit. Typically, bags containing saline solution are brought to the apparatus and used for priming. In a dialysis clinic with many dialysis machines, large amounts of saline solution are consumed and a significant number of heavy saline solution bags need to be stored and handled by staff. The use of prefabricated saline solution also adds to the cost of treatment, and transportation of bags with saline solution to dialysis clinics has a negative impact on the environment.

Some modern dialysis machines can perform so-called on-line treatment, in which substitution fluid for hemofiltration or hemodiafiltration is prepared inside the dialysis machine on-line by means of ultrafiltration of treatment fluid (dialysis fluid) in several steps to obtain a sterile and pyrogen free fluid. On-line prepared substitution fluid can be prepared in practically unlimited quantities which means that this fluid also may be used for priming, which is convenient from a handling point of view. However, modern dialysis machines with on-line capability are costly, with respect to both purchase and maintenance.

Thus, for cost reasons, many clinics are reluctant to replace older and/or simpler dialysis machines without on-line capability with more advanced dialysis machines.

Further, conventional priming involves many manual steps to be performed by attending staff and involves a risk of spilling priming fluid at and around the dialysis machine.

SUMMARY

It is an objective of the invention to at least partly overcome one or more limitations of the prior art.

A further objective is to facilitate access to a fluid suitable for priming of a blood treatment apparatus.

Another objective is to facilitate the process of priming a blood treatment apparatus, e.g. with respect to manual handling and/or spillage.

One or more of these objectives, as well as further objectives that may appear from the description below, are at least partly achieved by a control system, a blood treatment apparatus, a method, a computer-readable medium, and a disposable arrangement, embodiments thereof being defined by the dependent claims.

A first aspect of the invention is a control system for a blood treatment apparatus. The control system is configured to: instruct an operator to install a first flow circuit for conducting a fluid provided by the blood treatment apparatus through a dialyzer; instruct the operator to install a second flow circuit which is separated from the first flow circuit by a semi-permeable membrane of the dialyzer and comprising connectors for connection to a vascular system of a subject during blood treatment, wherein the second flow circuit is installed to be disconnected from the vascular system and form a closed loop that includes a sterilizing filter; operate the blood treatment apparatus to pump a human-compatible fluid into the first flow circuit so that a portion of the human-compatible fluid flows through the semi-permeable membrane into the second flow circuit; and operate the blood treatment apparatus to circulate said portion of the human-compatible fluid in the closed loop of second flow circuit, to thereby sterilize said portion of the human-compatible fluid by the sterilizing filter.

The first aspect improves access to sterile fluid for use in priming of a blood treatment apparatus, by the provision of a sterilizing filter in the closed loop formed by the second flow circuit before blood treatment. Specifically, the first aspect enables any blood treatment apparatus that is capable of supplying a human-compatible fluid to produce such a sterile fluid, even if the human-compatible fluid as such is not sufficiently sterile for use in priming. Further, the first aspect serves to facilitate the priming as such. By arranging the second flow circuit to form a closed loop that includes the sterilizing filter during priming, the human-compatible fluid may be sterilized by being circulated along the closed loop, and ultimately the closed loop will be flushed by sterile fluid. By forming the closed loop, the first aspect has the ability to reduce spillage during priming and may also reduce the number of manual operations required. The first aspect further facilitates priming by operating the blood treatment apparatus to pump the human-compatible fluid from the first flow circuit into the second flow circuit via the semi-permeable membrane of the dialyzer. This reduces the complexity of the priming by reducing the need for manual intervention in order to provide the human-compatible fluid to the second fluid circuit, and also reduces the risk of spillage.

In the following, various embodiments of the first aspect are defined. These embodiments provide at least some of the technical effects and advantages described in the foregoing, as well as additional technical effects and advantages as readily understood by the skilled person, e.g. in view of the following detailed description.

In one embodiment, in which the second flow circuit is installed to further include a container, the control system is further configured to: operate the blood treatment apparatus to collect a sterile fluid in the container, wherein the sterile fluid is generated by circulating said portion of the human-compatible fluid in the closed loop.

In one embodiment, said portion of the human-compatible fluid is circulated through the container.

In one embodiment, the control system is configured to instruct the operator to form the closed loop by directly or indirectly connecting the connectors to an inlet port and an outlet port, respectively, on the container.

In one embodiment, the second flow circuit is installed with the sterilizing filter being co-located with the outlet port so that said portion of the human-compatible fluid flows through the sterilizing filter when leaving the container via the outlet port.

In one embodiment, the second flow circuit is installed with the sterilizing filter directly or indirectly connected to one of the inlet and outlet ports of the container.

In one embodiment, the second flow circuit is installed with the sterilizing filter located within the container.

In one embodiment, in which the inlet and outlet ports define an inlet opening and an outlet opening, respectively, inside the container, the control system is configured to instruct the operator to install the second flow circuit such that the container locates the inlet opening above the outlet opening.

In one embodiment, the control system is further configured to instruct the operator to connect the connectors to the vascular system of the subject, and operate the blood treatment apparatus to perform said blood treatment, the control system being further configured to, subsequent to said blood treatment, instruct the operator to establish fluid communication between the container holding the sterile fluid and the second flow circuit, and operate the blood treatment apparatus to drive blood in the second flow circuit back into the vascular system of the subject while drawing at least a portion of the sterile fluid in the container into the second flow circuit.

In one embodiment, the control system is further configured to: instruct the operator to connect the connectors to the vascular system of the subject and install the container holding the sterile fluid for fluid communication with the second flow circuit, the control system being further configured to: operate the blood treatment apparatus to perform said blood treatment, and to introduce of a portion of the sterile fluid in the container into the second flow circuit during said blood treatment.

In one embodiment, the control system is further configured to ventilate the second flow circuit to expel gaseous substances.

In one embodiment, the control system is configured to circulate said portion of the human-compatible fluid in the closed loop of the second flow circuit so that said portion of the human-compatible fluid is passed at least once through the sterilizing filter.

In one embodiment, the control system is further configured to, while the human-compatible fluid is pumped into the first flow circuit, cause a flow restriction in the first flow circuit downstream of the dialyzer.

In one embodiment, the control system is configured to circulate said portion of the human-compatible fluid in the closed loop of the second flow circuit for a predefined time period after completion of said pumping.

In one embodiment, the human-compatible fluid comprises one of a saline solution, a treatment fluid for use during said blood treatment, and water.

A second aspect of the invention is a blood treatment machine. The blood treatment apparatus comprises a fluid supply unit configured to supply a human-compatible fluid to a first flow circuit when connected to the blood treatment apparatus, a pump operable to engage with a second flow circuit when connected to the blood treatment apparatus, and the control system of the first aspect or any of its embodiments.

A third aspect of the invention is a method of preparing a blood treatment apparatus for blood treatment. The method comprises: installing a first flow circuit for conducting a fluid provided by the blood treatment apparatus through a dialyzer; installing a second flow circuit which is separated from the first flow circuit by a semi-permeable membrane of the dialyzer and comprising connectors for connection to a vascular system of a subject during blood treatment, wherein the second flow circuit is installed to be disconnected from the vascular system and form a closed loop that includes a sterilizing filter; pumping, before blood treatment and by the blood treatment apparatus, a human-compatible fluid into the first flow circuit so that a portion of the human-compatible fluid flows through the semi-permeable membrane into the second flow circuit; and circulating, before blood treatment and by the blood treatment apparatus, said portion of the human-compatible fluid in the closed loop of second flow circuit, to thereby sterilize said portion of the human-compatible fluid by the sterilizing filter.

In one embodiment, in which the second flow circuit is installed to further include a container, the method further comprises: operating the blood treatment apparatus to collect a sterile fluid in the container, the sterile fluid being generated by said circulating.

In one embodiment, said portion of the human-compatible fluid is circulated through the container.

In one embodiment, in which the container comprises an inlet port and an outlet port, the second flow circuit is installed with the inlet and outlet ports being directly or indirectly connected to a respective one of the connectors.

In one embodiment, the second flow circuit is installed with the sterilizing filter being co-located with the outlet port so that said portion of the human-compatible fluid flows through the sterilizing filter when leaving the container via the outlet port.

In one embodiment, the second flow circuit is installed with the sterilizing filter being directly or indirectly connected to one of the inlet and outlet ports.

In one embodiment, the second flow circuit is installed with the sterilizing filter being located within the container.

In one embodiment, in which the inlet and outlet ports define an inlet opening and an outlet opening, respectively, inside the container, the second flow circuit is installed such that the container locates the inlet opening above the outlet opening.

In one embodiment, the method further comprises: ventilating the second flow circuit so as to expel gaseous substances during or after said circulating.

In one embodiment, said circulating is performed so that said portion of the human-compatible fluid is passed at least once through the sterilizing filter.

In one embodiment, the method further comprises, during said pumping, providing a flow restriction in the first flow circuit downstream of the semi-permeable filter.

In one embodiment, said circulating is performed for a predefined time period after completion of said pumping.

A fourth aspect is a computer-readable medium comprising computer instructions which, when executed by a processor, cause the processor to perform the method of the third aspect and any of its embodiments.

A fifth aspect of the invention is a disposable arrangement for use in a blood treatment apparatus. The disposable arrangement comprises: at least one fluid-conducting device which is configurable to define a flow circuit that extends through a blood chamber of a dialyzer and comprises connectors for connection to a vascular system of a subject during blood treatment. The disposable arrangement further comprises a sterilizing filter and being configurable to define the flow circuit to form a closed loop that includes the sterilizing filter.

In one embodiment, the disposable arrangement further comprises a container and is further configurable to define the flow circuit to include the container.

In one embodiment, the container comprises an inlet port and an outlet port, and the disposable arrangement is further configurable to include the container in the closed loop by connection, indirectly or directly, of the connectors to the inlet and outlet ports.

In one embodiment, the disposable arrangement is further configurable to co-locate the sterilizing filter with the outlet port so that said portion of the human-compatible fluid flows through the sterilizing filter when leaving the container via the outlet port.

In one embodiment, the disposable arrangement is further configurable to locate the sterilizing filter intermediate the container and one of the connectors.

In one embodiment, the sterilizing filter is arranged inside the container.

In one embodiment, the disposable arrangement further comprises a dialyzer. The dialyzer comprises a fluid chamber, the blood chamber, and a semi-permeable membrane separating the fluid and blood chambers, wherein the fluid chamber is configured for connection to a fluid supply unit of the blood treatment apparatus.

In one embodiment, the disposable arrangement is sterilized and located within one or more protective casings.

In one embodiment, which is applicable to all aspects, the sterilizing filter is a sterilizing-grade filter which is configured for bacterial retention and, preferably, for bacterial endotoxin retention.

Still other objectives, features, embodiments, aspects and advantages of the present invention may appear from the following detailed description, from the attached claims as well as from the drawings.

BRIEF DESCRIPTION OF THE DRAWINGS

Embodiments of the invention will now be described in more detail with reference to the accompanying drawings.

DETAILED DESCRIPTION OF EXAMPLE EMBODIMENTS

Figure 1A:
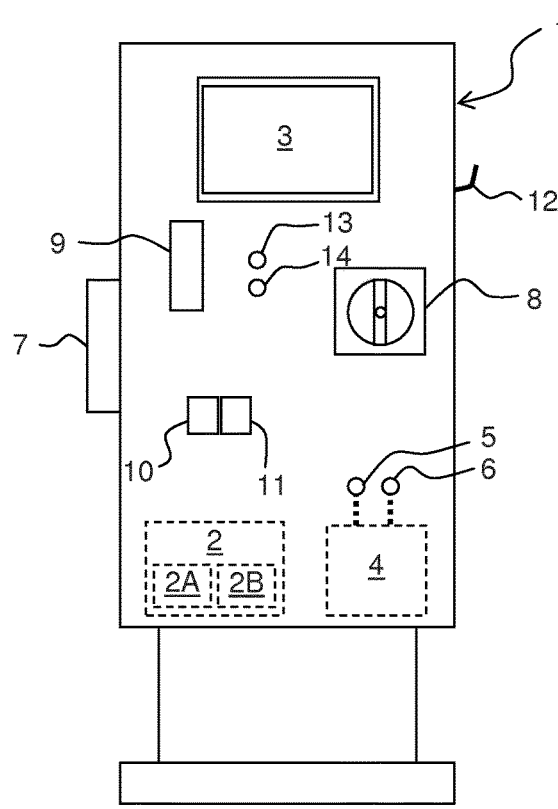
FIG. 1A is a schematic front view of a dialysis machine.

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention.

As used herein, "human-compatible fluid" refers to any fluid, which by its composition, and when sufficiently sterilized, is compatible with the human body if administered to its circulatory system in amounts relevant for the particular application. For example, the human-compatible fluid may be any such fluid that is available at a blood treatment apparatus, including but not limited to a physiological saline solution, a treatment fluid, and water.

As used herein, "sterile fluid" refers to any fluid with a sufficient sterility to be administered to the circulatory system of a mammal.

As used herein, "indirectly connected" denotes that two components are connected with each other via one or more intermediate components.

As used herein, a "sterilizing filter" is any filter capable of producing a sterile fluid by filtration. In one embodiment, the sterilizing filter is further arranged to produce a sterile and non-pyrogenic fluid. In one embodiment, the sterilizing filter is a sterilizing-grade filter, which is configured for bacterial retention and, optionally, also for bacterial endotoxin retention. In one embodiment, the sterilizing filter is a validated sterilizing-grade filter, i.e. a sterilizing filter that has passed a filter qualification process for demonstrating bacterial retention of the filter, e.g. using the well-known standard *Brevundimonas diminuta*, or any other standardized or non-standardized filter qualification process. In one embodiment, the sterilizing grade filter is arranged to filter the human-compatible fluid into a sterile fluid with an amount of bacteria that is zero Colony-Forming Units/mL (CFU/mL) and an amount of bacterial endotoxins that is less than 0.05 Endotoxin Units/mL (EU/mL). In one embodiment, the sterilizing grade filter includes a membrane having pores with average diameters suitable to produce sterile fluid, including the capability of removing endotoxins. In one example, the mean pore diameter for the sterilizing grade filter is less than 1 μm, such as 0.1-0.5 μm, e.g. 0.1 or 0.2 μm. Bacteria typically have a diameter of a few micrometers, and will then not pass through the pores. The filter membrane may further comprise a high molecular weight additive bearing cationic charges, for example a cationic charged polymer. Examples of other kinds of positively charged additives can be found in EP1710011. In such examples, the filter membrane will be positively charged and thus reject bacterial endotoxins, whereby less bacteria and bacterial endotoxins will pass the membrane. In an exemplary embodiment, bacteria and bacterial endotoxins may also be retained based on adsorption to the membrane. The membrane may be polyethersulfone-based. Other suitable polymers may be AN69, PAN, PMMA, cellulose, etc. Suitable sterilizing grade filters may, for example, be Pall IV-5 or GVS Speedflow filters, or be filters provided by the present applicant.

In the following, embodiments of the invention will be exemplified with reference to an apparatus configured for treatment of chronic renal failure, denoted "dialysis machine" below.

Figure 1B:
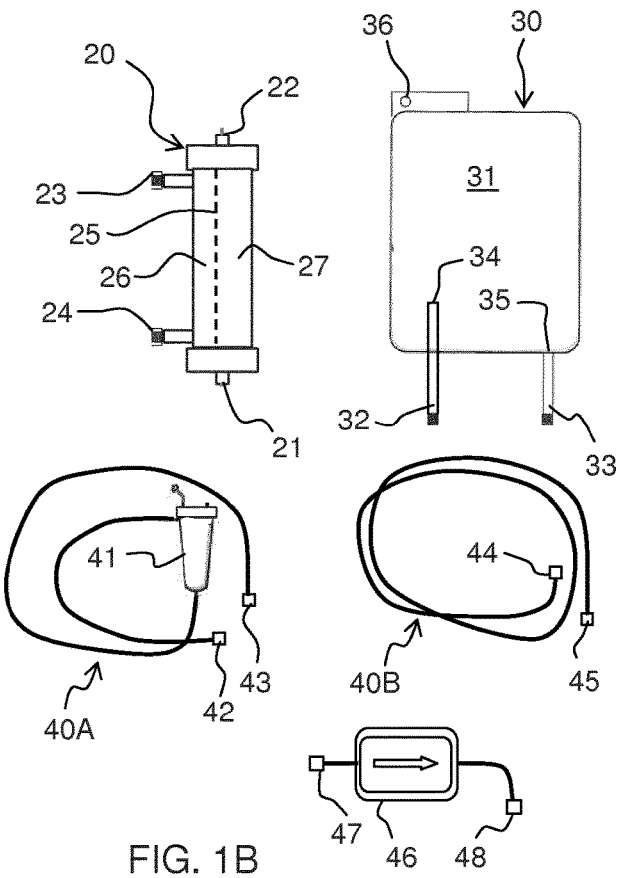
FIG. 1B illustrates a set of disposable products that may be connected in fluid communication with the dialysis machine.

FIG. 1A shows an example of such a dialysis machine 1, which is operable to perform a dialysis treatment when combined with a set of disposable products or "disposables", shown in FIG. 1B. The dialysis machine 1 in FIG. 1A is also known as "monitor" and defines a machine chassis that exposes holders for mounting the disposable(s) in operative engagement with components such as connectors, pumps, sensors, clamps, etc. The disposables are exposed to circulating blood and are typically for single-use, i.e. they are discarded after each treatment session.

In the illustrated example, a control system or controller 2 in the machine 1 is configured to synchronize and control the operation of the components of the machine 1, e.g. by electric control signals. The operation of the control system 2 may be at least partly controlled by software instructions that are supplied on a computer-readable medium for execution by a processor 2A in conjunction with a memory 2B in the control system 2. A display unit 3 is operable to provide information and instructions for a user, such as a nurse, a physician or a patient. The machine 1 may also enable the user to enter data into the machine, e.g. via mechanical buttons or keys, or virtual buttons or keys on a touch panel, e.g. in the display unit 3. A fluid supply unit 4 is configured to supply one or more suitable fluids during operation of the machine L Such fluids may include one of more of a treatment fluid (dialysis fluid) for use during blood treatment, a disinfectant for use in disinfection of the machine between treatments, a saline solution, and purified water. The fluids may be supplied from replaceable containers attached to the machine 1 or may be generated on demand by the machine 1 or another apparatus in fluid communication with the machine 1. In the illustrated example, the machine comprises two machine ports 5, 6 in fluid connection to the supply unit 4. The machine 1 further comprises a holder 7 for a dialyzer (20 in FIG. 1B), a peristaltic pump ("blood pump") 8 for engagement with a blood line, and holder 9 for a drip chamber (41 in FIG. 1B). The machine 1 further comprises two machine-controlled clamps 10, 11 for engagement with a respective blood line section. Further, a holder 12 is provided for a container (30 in FIG. 1B). In the illustrated example, the machine 1 also comprises sensor ports 13, 14 in fluid communication with pressure sensors (not shown) within the machine 1. The skilled person realizes that the machine 1 may comprise further components that are not shown in FIG. 1A, e.g. a blood detector, an injection system for anticoagulant, etc.

The set of disposables in FIG. 1B includes the above-mentioned dialyzer 20, which is a blood filtration unit comprising inlet and outlet connectors 21, 22 for fluid connection to blood lines (below), and inlet and outlet connectors 23, 24 for connection to the machine ports 5, 6.

A semi-permeable membrane 25 ("dialyzer membrane") is arranged inside the housing of the dialyzer 20 to separate a first chamber ("dialysis fluid side compartment") 26 from a second chamber ("blood side compartment") 27. The first and second chambers 26, 27 are configured to be perfused by blood and dialysis fluid, respectively, during blood treatment. The set of disposables in FIG. 1B also includes a container 30, which may be made of rigid or flexible material, preferably a transparent or translucent material that allows for ocular inspection of the contents in the container 30. The container 30 defines an interior fluid collecting space 31 and comprises an inlet port 32 and an outlet port 33, which are in fluid communication with the fluid collecting space 31. The ports 32, 33 define an inlet opening 34 and an outlet opening 35, respectively, inside the container 30. In the illustrated example, the container 30 further defines a suspension hole 36. The disposables in FIG. 1B further include fluid-conducting devices in the form of first and second line arrangements 40A, 40B, which are collectively known as a "line set" in the art. The first line arrangement 40A comprises a drip chamber 41 and flexible tubing that defines a flow path from a first end with a dialyzer connector 42 to a second end with a patient connector 43. The second line arrangement 40B comprises flexible tubing that defines a flow path from a first end with a patient connector 44 to a second end with a dialyzer connector 45. Although not shown in FIG. 1B, each of the line arrangements 40A, 40B may include further components, such as one or more manual clamps, tubing for connection to a pressure sensor (cf. sensor ports 13, 14 in FIG. 1A), tubing for injection of a fluid, etc. The disposables in FIG. 1B also include a sterilizing filter 46, which is configured to remove endotoxins, viruses and bacteria from a fluid when passing through the filter 46. The sterilizing filter 46 is provided with inlet and outlet connectors 47, 48.

The disposables in FIG. 1B are suitably sterilized and provided in one or more protective casings, e.g. a sealed bag, wrapping or package. It is conceivable that one or more disposables are interconnected within such a protective casing, and it is also conceivable that one or more of the above-mentioned connectors are replaced by permanent connections or joints between the disposables. For example, the filter 46 may be permanently connected to or integrated in the container 30, and the line arrangements 40A, 40B may be permanently connected to the dialyzer 20.

Figure 2:
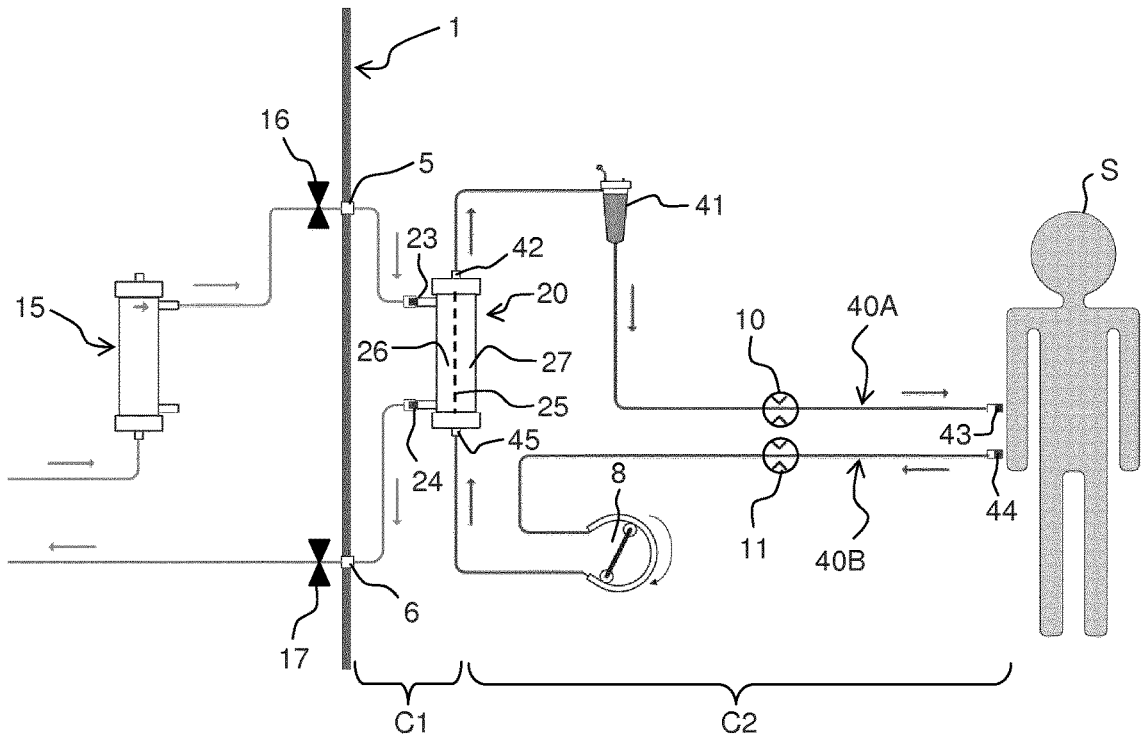
FIG. 2 is a schematic diagram of a dialysis machine connected and operated for blood treatment.

FIG. 2 illustrates a dialysis machine 1, e.g. as shown in FIG. 1A, which is connected to a set of disposables and operated for hemodialysis treatment of a subject S, in this example a human patient. As understood from FIG. 2, the disposables have been mounted to the machine 1 by attaching the dialyzer 20 to the holder 7 (FIG. 1A) and the drip chamber 41 to the holder 9 (FIG. 1A), and by arranging tubing of line arrangement 40B for engagement with the peristaltic pump 8 and tubing of the line arrangements 40A, 40B in the machine clamps 10, 11. The set of disposables is connected for fluid communication with the dialysis machine 1 so as to define a first flow circuit C1 ("dialysis fluid circuit") for dialysis fluid supplied by the dialysis machine 1 and a second flow circuit C2 ("extracorporeal blood circuit") which is connected to the vascular system of the subject S. Specifically, the dialyzer 20 is connected by the connectors 23, 24 for fluid communication with the ports 5, 6, thereby forming the first flow circuit C1. Further, the dialyzer 20 is connected by the connectors 21, 22 for fluid communication with the line arrangements 40A, 40B, thereby forming the second flow circuit C2. During blood treatment, the patient connectors 43, 44 are connected to a blood vessel access of the subject S. As is well-known in the art, the blood vessel access (also known as "vascular access") may be a fistula, graft or catheter, and the patient connectors 43, 44 may be connected to the blood vessel access by any conventional device, including needles or catheters. FIG. 2 also illustrates part of the flow path from the fluid supply unit 4 (FIG. 1A) to the ports 5, 6. The flow path includes an ultrafilter 15, which is permanently arranged inside the machine 1 and subject to replacement only during maintenance. Such an ultrafilter 15 is a standard component of most dialysis machines and serves to improve the purity of the dialysis fluid that is supplied by the machine 1, by removing biological contaminants such as endotoxins, viruses and bacteria. The machine 1 further includes machine-operated outlet and inlet valves 16, 17 for selectively opening and closing the ports 5, 6. In the following, filled and non-filled valve symbols indicate that a valve is open and closed, respectively.

In FIG. 2, the machine 1 is operated by the control system 2 (FIG. 1A) to open the valves 16, 17 and establish a flow of dialysis fluid through the first chamber 26 of the dialyzer 20, as indicated by arrows in FIG. 2. The machine 1 is also operated by the control system 2 to open the clamps 10, 11 and run the pump 8 so that blood is drawn from the vascular system of the subject S along line arrangement 40B, pushed through the second chamber 27 of the dialyzer 20 and back to the vascular subject S along line arrangement 40A, as indicated by arrows FIG. 2, while the blood is being subjected to dialysis treatment in the dialyzer 20. Dialysis treatment as such is well-known to the person skilled in the art and will not be further described herein.

Before the line arrangements 40A, 40B and the dialyzer 20 are utilized in any dialysis treatment, both should be primed. Priming is a process of replacing air with a sterile fluid in the line arrangements 40A, 40B and the dialyzer 20 by allowing the sterile fluid to flow through these components. Without priming, air may enter the vascular system of the subject S during treatment and cause air embolism. Further, excess air may lead to clotting of the dialyzer 20 during treatment, which may negatively affect the subject S. Priming is a time-consuming and often sloppy process that requires access to relatively large quantities of sterile fluid and involves several manual steps by the operator. Embodiments of the invention aim at facilitating priming.

During dialysis treatment, there may be a need to inject a quantity of a sterile fluid into the circulating blood in the second fluid circuit C2. For example, it is known to inject a bolus of a sterile hypertonic solution into the blood of the subject S to counteract hypertension, which is a common and severe intradialytic acute complication. Embodiments of the invention aim at facilitating access to a sufficiently sterile fluid for such injection.

When dialysis treatment is completed, it is common practice to return all or most of the blood remaining in the second flow circuit C2 to the vascular system of the subject S. This process is known as "rinse back" and involves introducing a fluid into the second flow circuit C2 so as to push back the remaining blood into the subject S. The fluid should be sterile since there is a risk of fluid entering the vascular system during rinse back. Embodiments of the invention aim at facilitating access to a sufficiently sterile fluid for rinse back.

By insightful reasoning, the inventors have found that it is possible use any human-compatible fluid supplied by the dialysis machine 1 as a priming fluid by introducing a sterilizing filter (cf. 46 in FIG. 1B) in the second flow circuit C2 during priming, and that priming may be greatly facilitated if the second flow circuit C2 is arranged to form a closed loop that includes the sterilizing filter during priming. The human-compatible fluid may thereby be sterilized by being circulated along the closed loop, while at the same time flushing the closed loop. By venting the closed loop, it may be ensured that the closed loop is sufficiently free of air. This novel process has the ability to reduce spillage during priming and may also reduce the number of manual operations required. Further, it enables priming by use of a fluid supplied by the dialysis machine 1, even if this fluid does not have the required sterility. It should be understood that the requirement of sterility is generally less strict with respect to the first flow circuit C1 compared to the second flow circuit C2, since the former will not be in physical contact with the vascular system of the subject S during treatment. Thus, many dialysis machines are incapable of supplying a sufficiently sterile fluid for use in priming. To further facilitate priming, the dialysis machine 1 may be operated to supply the human-compatible fluid by so-called backfiltration through the dialyzer membrane 25, i.e. by pushing the human-compatible fluid from the first flow circuit C1 into the second flow circuit C2 through the dialyzer membrane 25. This will further reduce spillage and manual manipulation.

In one simple and user friendly implementation, the sterilizing filter is connected intermediate the patient connectors 43, 44 of the second flow circuit C2 to form a closed loop during priming. Thereby, the flow path of the human-compatible fluid in the second flow path C2 during priming corresponds to the flow path of blood during dialysis treatment. Thus, the entire blood path is primed in one operation, i.e. by the circulation of the human-compatible fluid in the closed loop.

The inventors have further realized that it may be advantageous to include a container (cf. 30 in FIG. 1B) in the second flow circuit C2 during priming and operate the dialysis machine 1 to collect a portion of the human-compatible fluid, after being sterilized by the sterilizing filter, in the container as part of the priming procedure. This allows the fluid in the container to be used during or after the dialysis treatment, e.g. for the above-mentioned bolus injection or rinse back. The sterilization of the human-compatible fluid ensures that the human-compatible fluid in the container has an appropriate sterility to be introduced into the second flow circuit C2 at the end of the dialysis treatment, which may be 4-8 hours after the initial priming.

The inventors have further realized that it may be advantageous to arrange the container in the second flow circuit C2 during priming such that it is included in the closed loop and the human-compatible fluid is circulated through the container. Thereby, it is possible to collect the sterilized human-compatible fluid in the container as part of the circulation, instead of performing a separate filling operation after circulation. Thus, the complexity of the process is reduced.

In one simple and user friendly implementation, the container has at least one inlet port and at least one outlet port, which are configured to be connected, directly or indirectly, to the patient connectors 43, 44 of the second flow circuit C2 during priming.

Figure 3:
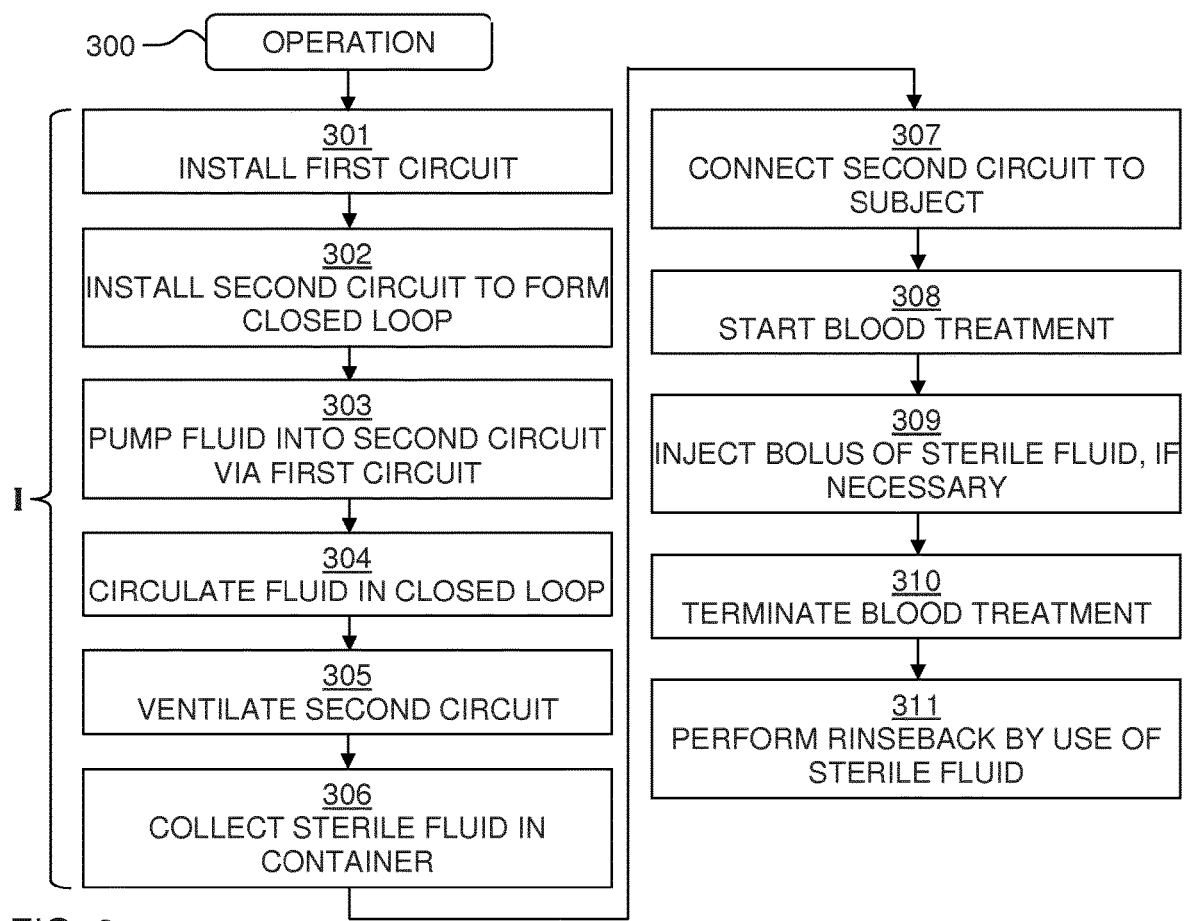
FIG. 3 is a flow chart of a method of operating a dialysis machine in accordance with an embodiment.

In the following, an embodiment of the invention will be described with reference to a flow chart in FIG. 3 in combination with system diagrams in FIGS. 4-6. The flow chart in FIG. 3 represents an operational method 300 that includes priming, dialysis treatment, optional bolus injection during dialysis treatment, and rinse back after completed treatment. Each of the steps 301-311 of the method 300 may be controlled by the control system 2 of the dialysis machine 1. To the extent that a step involves a manual operation, the control system 2 may generate and present corresponding instructions for the operator, e.g. on the display 3, and may also require the operator to confirm when the manual operation has been completed, e.g. by pressing or touching a button on the machine 1. However, as will be clarified below, it also conceivable that one or more of the steps are independently performed by the operator based on written instructions, e.g. from an operations manual or work guide, without involvement of the control system 2.

Figure 4:
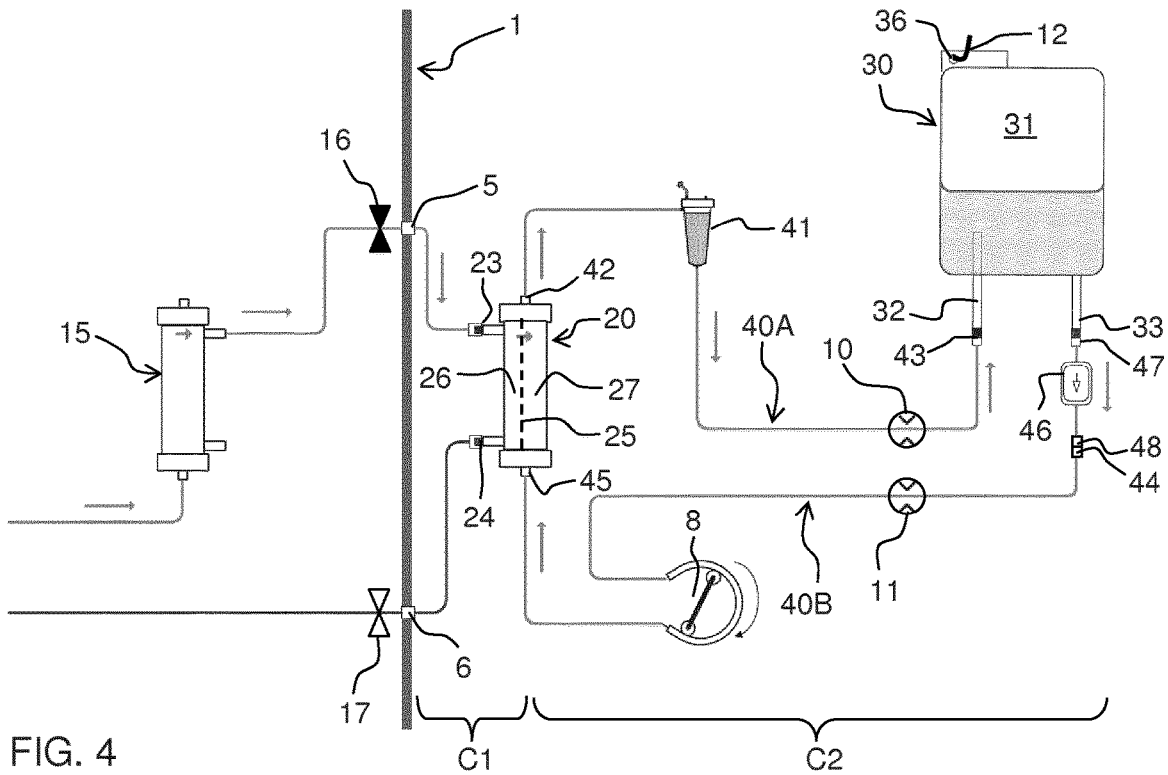
FIG. 4 is a schematic diagram of a dialysis machine connected and operated in preparation of blood treatment in accordance with an embodiment.
Figure 5A:
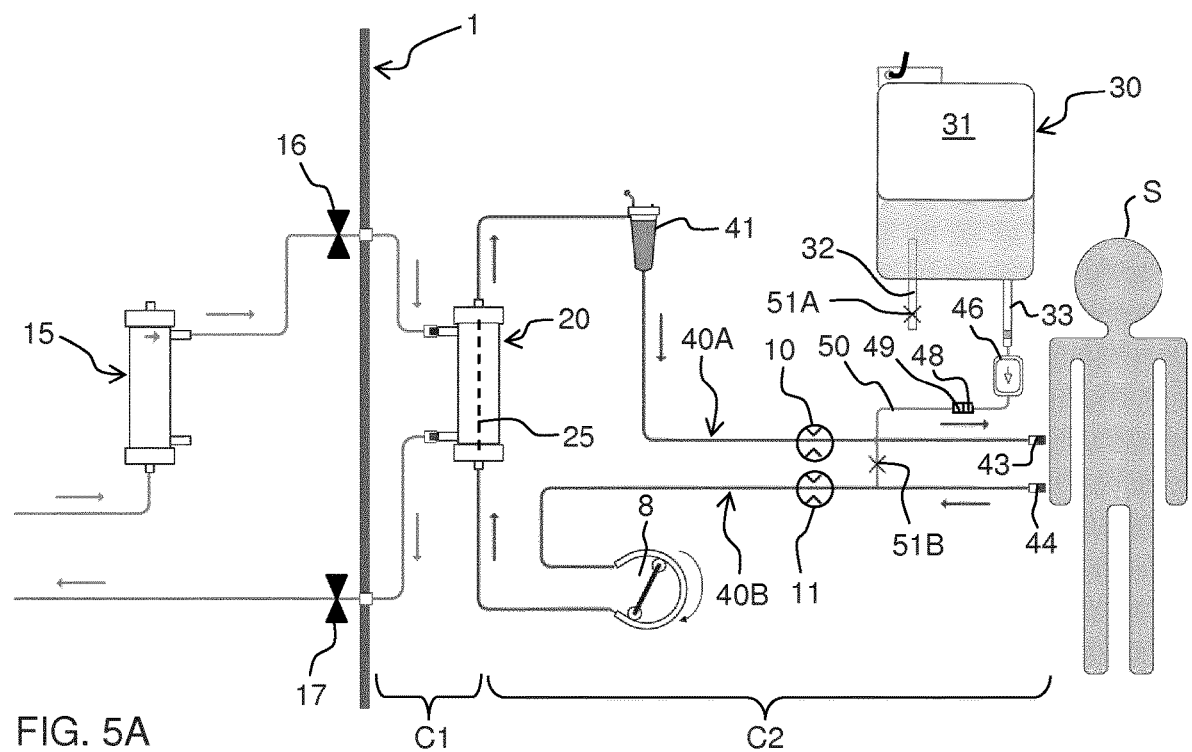
FIGS. 5A-5B is a schematic diagram of a dialysis machine connected and operated for bolus injection in accordance with an embodiment.
Figure 5B:
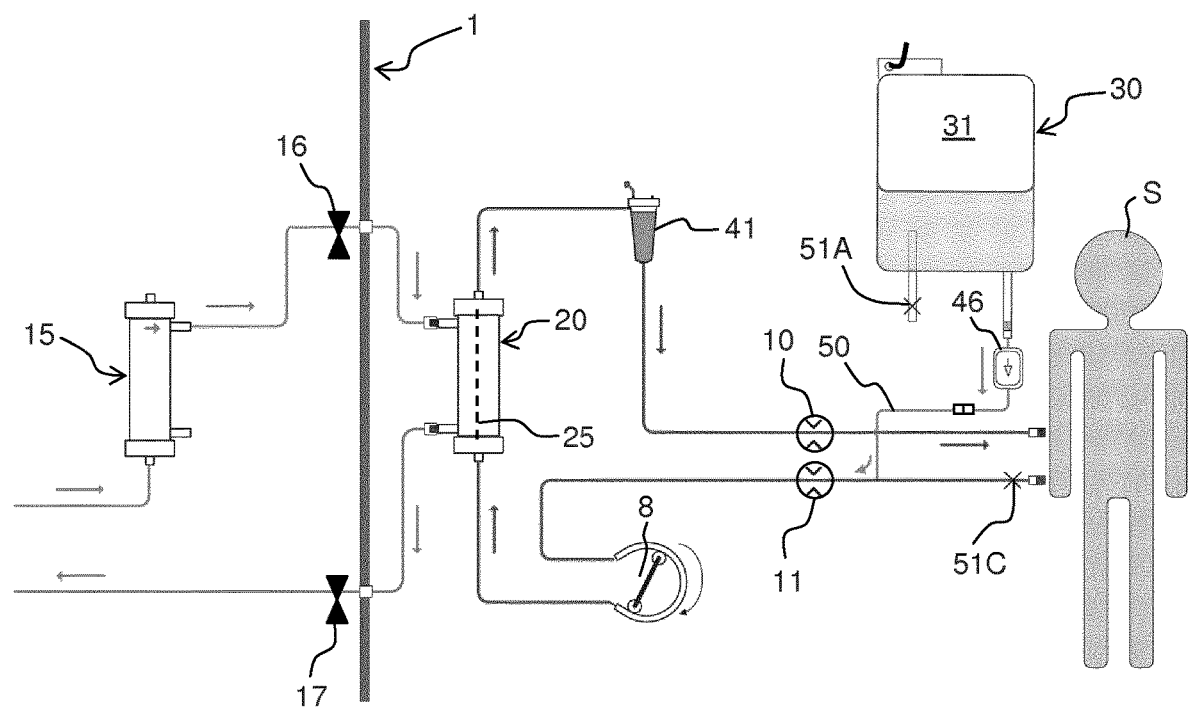

The system diagram in FIG. 4 illustrates a dialysis machine 1 when arranged and operated for priming. FIGS. 5A-5B illustrate a dialysis machine 1 when arranged and operated for bolus injection during dialysis treatment, and FIGS. 6A-6E illustrate different arrangements for rinse back after dialysis treatment.

Reverting to FIG. 3, steps 301-306 define a priming sequence I for the dialysis machine 1. In step 301, the first flow circuit C1 is installed on the dialysis machine 1, by the operator connecting the first chamber 26 of the dialyzer 20 for fluid communication with the fluid supply unit 4. In the example of FIG. 4, the inlet and outlet connectors 23, 24 are connected to the ports 5, 6 via tubing sections that may be permanently attached to the ports 5, 6 or be provided as disposables that are attached by the operator. In a further alternative, not shown, the ports 5, 6 may be located at the holder 7 so that the connectors 23, 24 engage the ports 5, 6 when the dialyzer 20 is mounted in the holder 7. Step 301 may be performed by the operator based on instructions provided by the control system 2 or independently based on written instructions.

In step 302, the second flow circuit C2 is installed on the dialysis machine 1 by use of the disposables in FIG. 1B, such that the second flow circuit C2 forms a closed loop that includes the filter 46 and the container 30. In view of the disposables in FIG. 1B, the operator would, in any order, arrange the suspension hole 36 of container 30 on holder 12, attach dialyzer connector 42 to outlet connector 22, arrange drip chamber 41 in holder 9, arrange tubing of line arrangement 40A in clamp 10, attach dialyzer connector 45 to inlet connector 21, arrange tubing of line arrangement 40B in engagement with pump 8 and in clamp 11, attach patient connector 43 to inlet port 32, attach inlet connector 47 to outlet port 33, and attach patient connector 44 to outlet connector 48. It is realized that the number of manual operations performed by the operator during step 302 depends on if and how the disposables are interconnected when delivered to the operator. Step 302 may be performed by the operator based on instructions provided by the control system 2 or independently based on written instructions.

In step 303, the dialysis machine 1 is operated to pump a human-compatible fluid (denoted "priming fluid" in the following) into the first flow circuit C1 such that a portion of the priming fluid passes through the dialyzer membrane 25 into the second flow circuit C2, as indicated by arrows in FIG. 4. This so-called backfiltration may be achieved by controlling the machine 1 to generate an excess pressure in the first chamber 26 compared to the second chamber 27. In FIG. 4, outlet valve 16 is opened during step 303 so that priming fluid is pumped into the first chamber 26 via port 5. As indicated in FIG. 4, valve 17 may be closed, or otherwise operated to increase flow resistance, to increase the pressure in the first chamber 26 and thereby speed up the process of pushing priming fluid into the second flow circuit C2.

In step 304, the dialysis machine 1 is operated to circulate the priming fluid along the closed loop of the second flow circuit C2, e.g. as indicated by arrows in FIG. 4. Step 304 may be initiated before step 303 is completed, although it is conceivable to perform steps 303, 304 in sequence. In the example of FIG. 4, the clamps 10, 11 are opened and the blood pump 8 is operated to circulate the priming fluid through the container 30 and the sterilizing filter 46. Step 304 is suitably performed until all of the priming fluid in the second flow circuit C2 has passed through the sterilizing filter 46 at least once, e.g. in accordance with a predefined time period. At the end of step 304, the second flow circuit C2 contains a sterile fluid.

In step 305, which may be performed at any time during step 304 or thereafter, the second flow circuit C2 is ventilated to expel excess air, e.g. via the drip chamber 41 or the container 30. For example, the operator may be instructed by the control system 2 to open a dedicated clamp or valve (not shown). Alternatively, the control system 2 may generate a control signal for opening such a clamp or valve. Optionally, the ventilation may be assisted by a pump (not shown) in the machine 1, which is connected for fluid communication with the second fluid circuit C2 and operated based on a control signal from the control system 2. It is also conceivable that the second flow circuit C2 is pre-configured to be open to the surroundings, e.g. via the drip chamber 41 or the container 30, when it is installed in step 302.

In step 306, the sterile fluid is collected in the container 30. In the example of FIG. 4, step 306 is performed as part of step 304, since the priming fluid is circulated via the container 30 and is gradually converted into the sterile fluid after passing the sterilizing filter 46. However, in other embodiments, step 306 may be a separate step performed after step 304 and/or step 305. By collecting the sterile fluid in the container 30, it is possible to make further use of the sterile fluid during or after the dialysis treatment.

It is realized that the arrangement of disposables in FIG. 4 enables the second flow circuit C1 to be primed essentially without spillage and without intervention of the operator, except for the installation of the disposables on the dialysis machine 1.

When the priming sequence I is completed, the operator may be instructed to connect the second flow circuit C2 to the subject S (step 307). In the example of FIG. 4, the operator may close the ports 32, 33 of the container, e.g. by use of manual clamps, disconnect the patient connectors 43, 44 from the inlet port 32 and the outlet connector 48, and connect the patient connectors 43, 44 to the vascular access of the subject S in accordance with common practice, resulting in the arrangement shown in FIG. 2. Then, in step 308, the control system 2 may start the dialysis treatment.

If a need arises, for any reason, to introduce a sterile fluid into the circulatory system of the subject S, e.g. to counteract hypertension, the operator may be given the possibility of introducing one or more dosages ("boluses") of sterile fluid from the container 30 into the second flow circuit C2 (step 309). An example is shown in FIGS. 5A-5B, in which the line arrangement 40B has a branch line 50 which connects to the blood line that extends between the connectors 44, 45. Conventionally, most line sets include at least one such branch line, e.g. denoted service line or infusion line. In the example of FIG. 5A, a connector 49 at the end of the branch line 50 has been connected, e.g. during step 307, to the outlet connector 48, and thus in fluid communication with the outlet port 33 of the container 30, while the inlet port 32 is closed by a clamp 51A and the branch line 50 is closed by a clamp 51B. When there is need for a bolus injection, e.g. as detected by the control system 2 based on data from one or more sensors (not shown), by the operator or by the subject S, the arrangement in FIG. 5A may be modified in accordance with FIG. 5B. Thus, the clamp 51B may be opened, manually or by the control system 2, to admit a bolus of sterile fluid into the second flow circuit C2 while the blood pump 8 is active. As indicated in FIG. 5B, the blood line may be temporarily closed upstream of the connection to the branch line 50, to increase the suction force of the blood pump 8 in the branch line 50 and thereby shorten the time required to introduce the bolus. In an alternative configuration, not shown, the connection of the branch line 50 to the blood line may be located downstream of the clamp 11. The foregoing procedure is equally applicable to this configuration, although it is conceivable that the clamp 51C is omitted and the suction force in the branch line 50 is instead increased by closing the clamp 11.

Reverting to FIG. 3, at step 310, the dialysis machine 1 terminates the dialysis treatment. This may involve stopping the supply of dialysis fluid to the dialyzer 20 by closing the valves 16, 17 (FIG. 2), stopping the blood pump 8, and closing the clamps 10, 11. The operator is then instructed to perform a rinse back procedure by use of the sterile fluid in the container 30 (step 311). The implementation of the rinse back procedure may differ depending on the configuration of the second flow circuit C2.

Figure 6A:
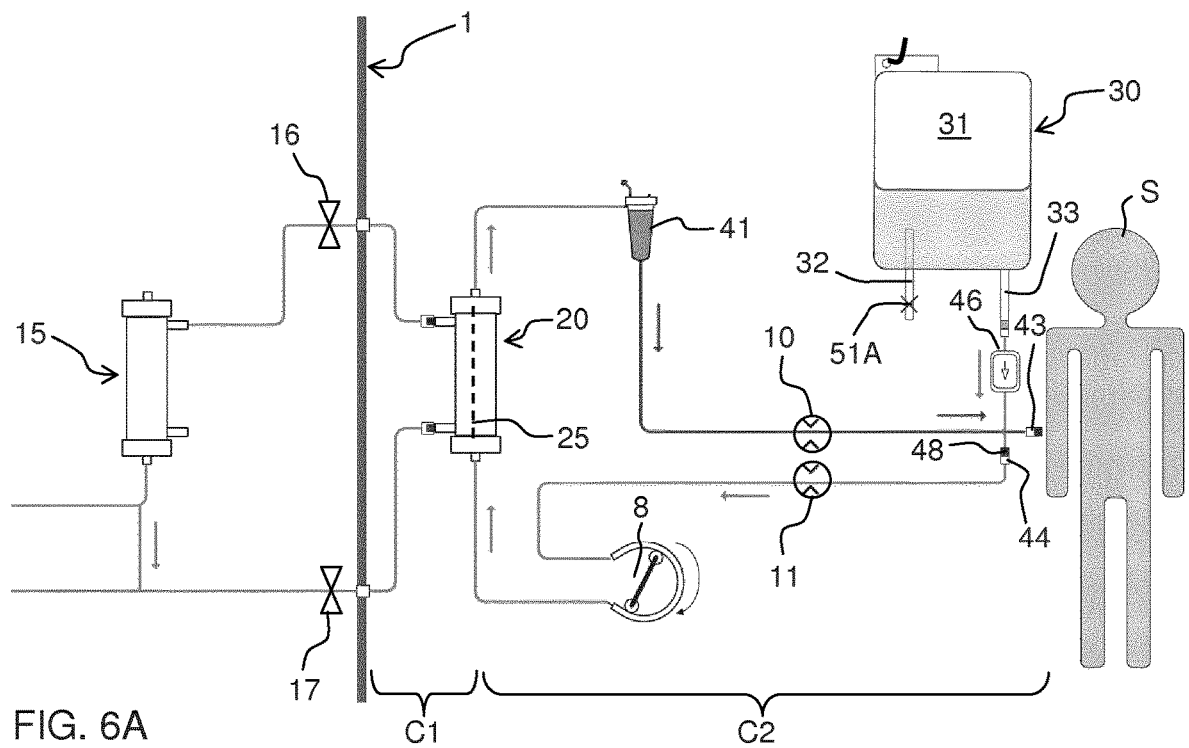
FIGS. 6A-6E are schematic diagrams of a dialysis machine connected and operated for rinse-back in accordance with different embodiments.

One implementation, which does not require a branch line 50, is shown in FIG. 6A. Here, the operator is instructed to disconnect the patient connector 44 from the vascular access and connect the patient connector 44 to the outlet connector 48, and thereby in fluid communication with the outlet port 33 of the container 30. The dialysis machine 1 then opens the clamps 10, 11 and operates the blood pump 8 to push the remaining blood in the second flow circuit C2 into the subject S while drawing sterile fluid from the container 30, as indicated by arrows in FIG. 6A, until all or a majority of the remaining blood in the second flow circuit C2 has been returned to the subject S. The configuration in FIG. 6A requires a minimum of operations and minimizes the risk of spillage.

Figure 6B:
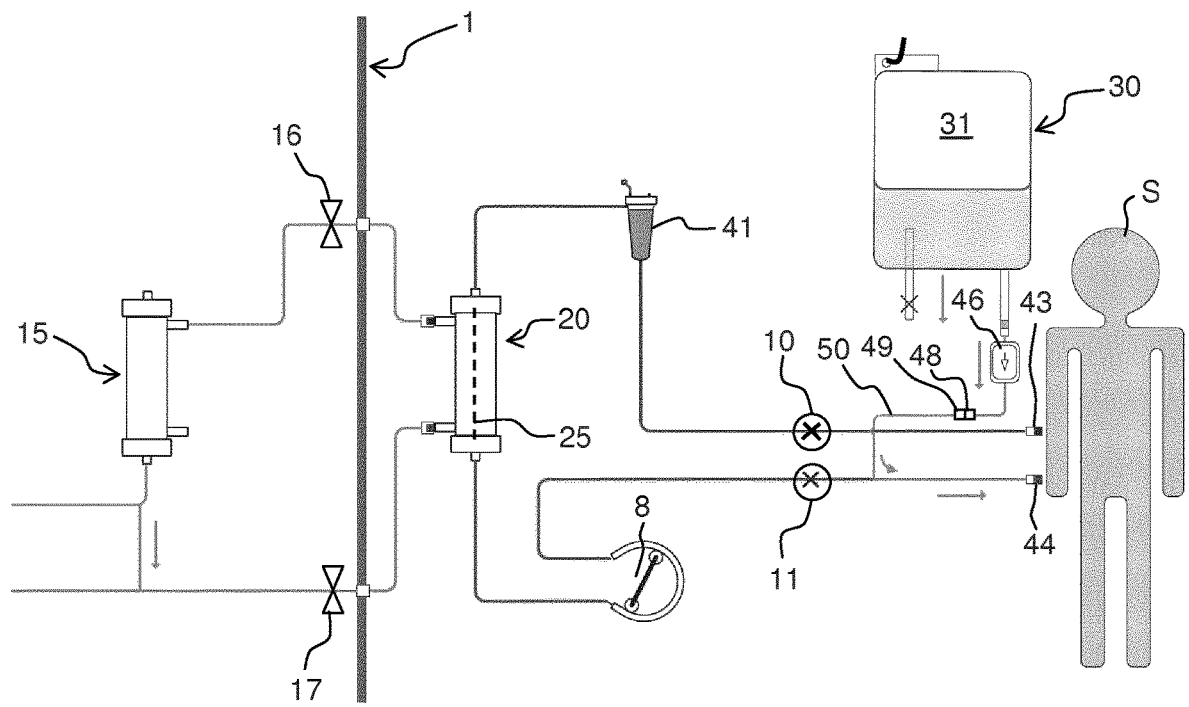
Figure 6C:
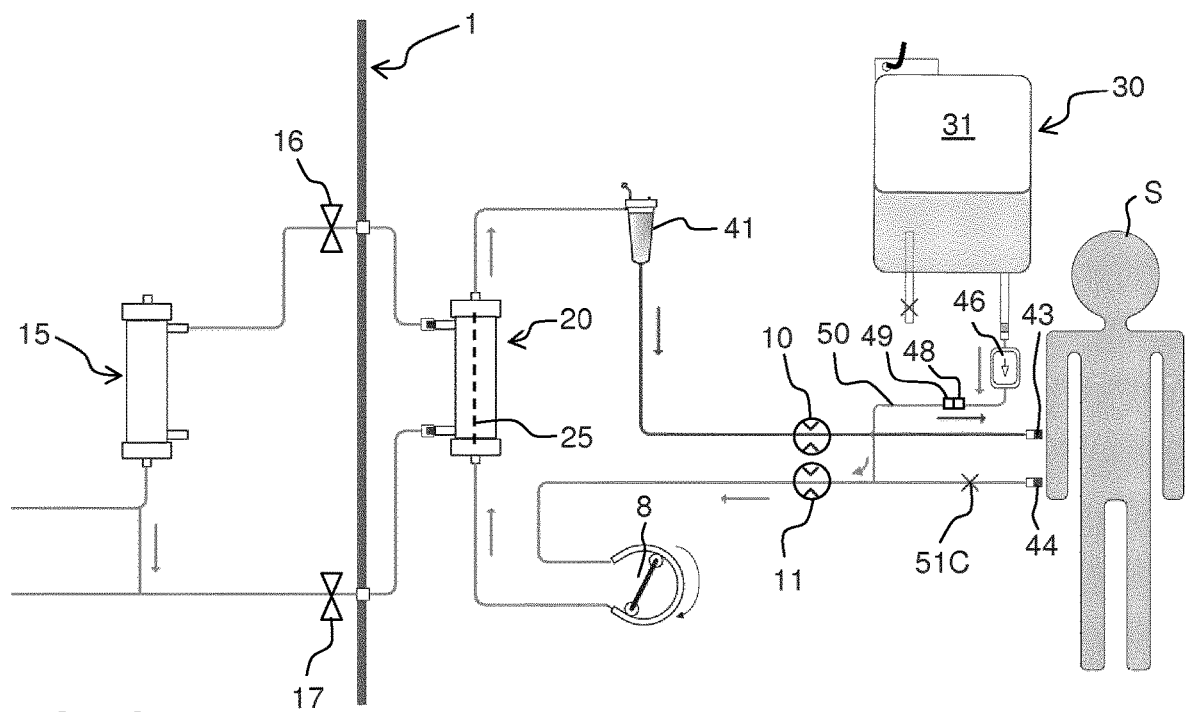

If the line arrangement 40B has a branch line 50 between the clamp 11 and the patient connector 44, the implementation in FIGS. 6B-6C may be convenient. Here, the operator is instructed to connect the connector 49 to the outlet connector 48, if not already connected during the dialysis treatment (cf. FIGS. 5A-5B). In a first phase, shown in FIG. 6B, while the clamps 10, 11 remain closed and the blood pump 8 remains stopped, the operator is instructed to remove the clamp 51B (FIG. 5A), if present. Thereby, sterile fluid is driven by gravity along the branch line 50 into the second flow circuit C2 to push blood back into the subject S, as indicated by arrows in FIG. 6B. In a second phase, shown in FIG. 6C, the operator is instructed to close the line arrangement 40B between the branch line 50 and the patient connector 44, e.g. by use of a clamp 51C. The dialysis machine 1 then opens the clamps 10, 11 and operates the blood pump 8 to push the remaining blood in the second flow circuit C2 into the subject S while drawing sterile fluid from the container 30, as indicated by arrows in FIG. 6C.

Figure 6D:
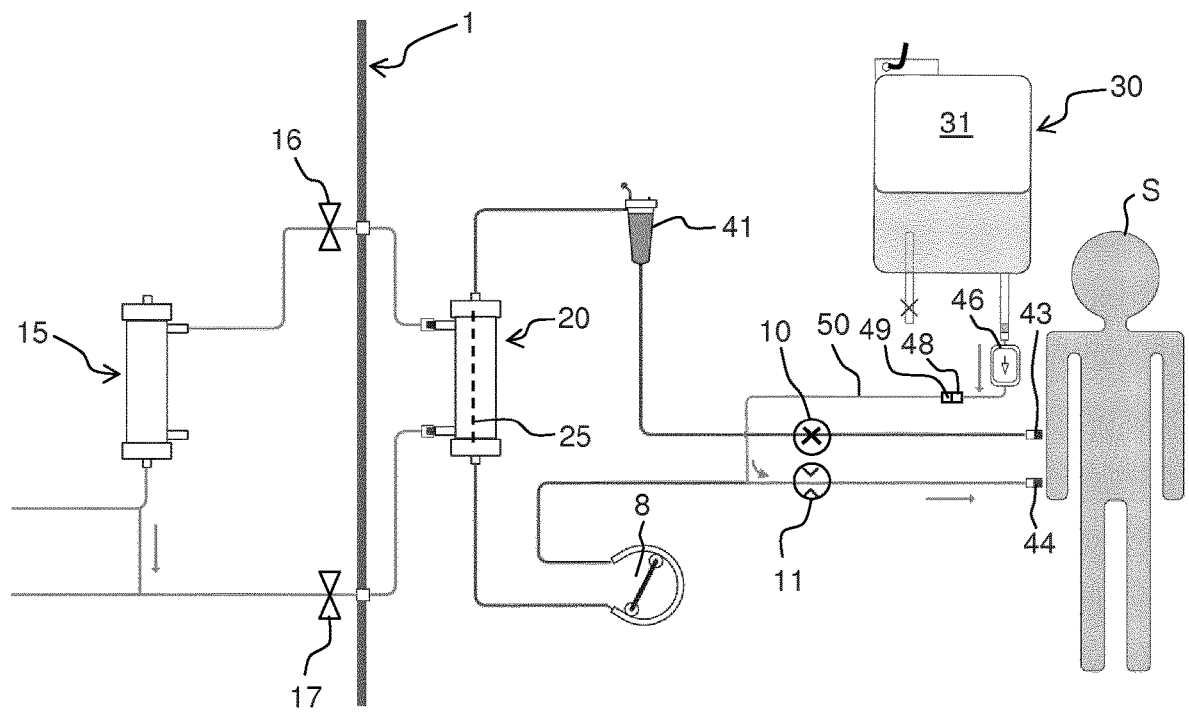
Figure 6E:
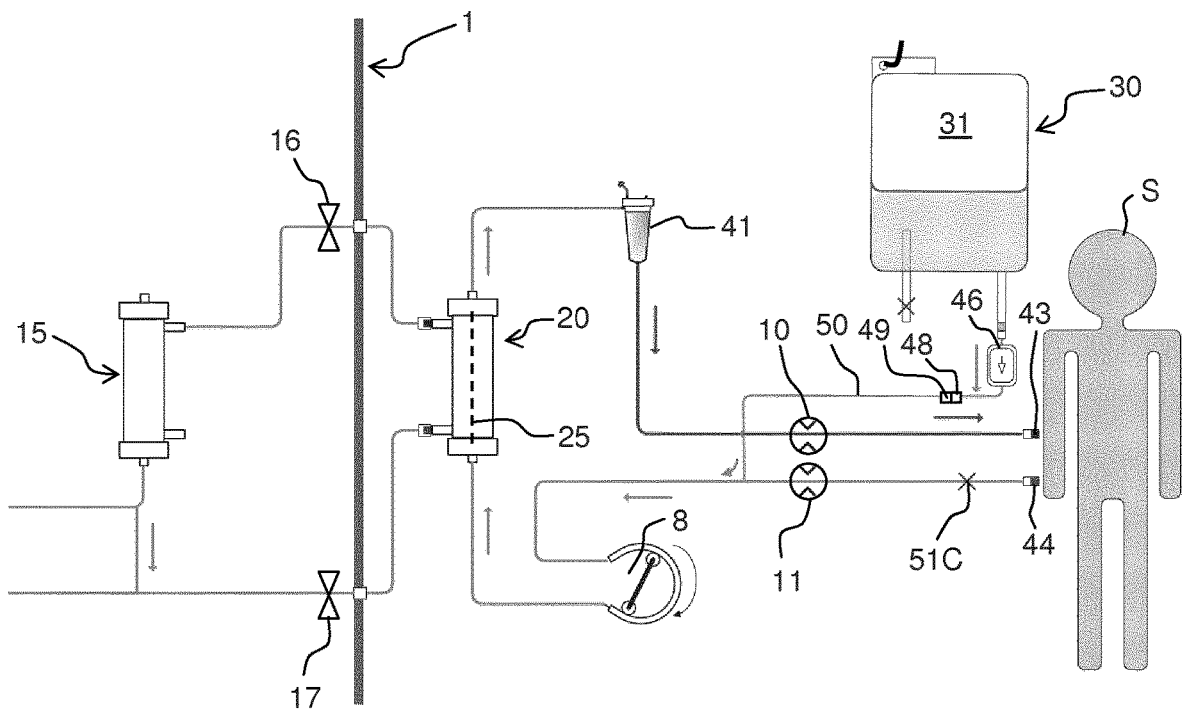

If the line arrangement 40B has a branch line 50 between the clamp 11 and the blood pump 8, the implementation in FIGS. 6D-6E may be convenient. Here, the operator is instructed to connect the connector 49 to the outlet connector 48, if not already connected during the dialysis treatment. In a first phase, shown in FIG. 6D, the operator is instructed to remove the clamp 51B (if present, cf. FIG. 5A) from the branch line 50. The dialysis machine 1 is operated to open clamp 11, while the blood pump 8 remains stopped. Thereby, sterile fluid is driven by gravity along the branch line 50 into the second flow circuit C2 to push blood back into the subject S, as indicated by arrows in FIG. 6D. In a second phase, shown in FIG. 6E, the operator is instructed to close the line arrangement 40B between the clamp 11 and the patient connector 44, e.g. by use of a clamp 51C. The dialysis machine 1 then opens clamp 10 and operates the blood pump 8 to push the remaining blood in the second flow circuit C2 into the subject S while drawing sterile fluid from the container 30, as indicated by arrows in FIG. 6E. In a variant, the clamp 51C is omitted, and the clamp 11 is closed by the dialysis machine 1.

It may be noted that the container 30 is configured such that the inlet opening 34 is located above (in the direction of gravity) the outlet opening 35 when the container 30 is suspended during priming (FIG. 4). This feature has been found to significantly reduce the risk that air is drawn from the container 30 via the outlet port 35 into the line arrangement 40B when the priming fluid is circulated through the container 30, especially when a small amount of priming fluid is present in the container 30, e.g. at startup of step 303 and/or step 304 during the priming sequence I in FIG. 3.

In the illustrated embodiments, the sterilizing filter 46 is co-located with the outlet port 32 so that the fluid in the container 30 will flow through the filter 46 when leaving the container 30. This configuration ensures that the sterile fluid that is held in the container 30 after priming will be subjected to an additional sterilization when leaving the container 30, e.g. for bolus injection (FIGS. 5A-5B) or rinse back (FIGS. 6A-6E). This may increase the usable life of the sterile fluid in the container 30. It may be noted that the sterilizing filter 46 need not be arranged downstream of the outlet port 33, as shown, by may instead be arranged inside the container 30 to cover the outlet opening 35. In other embodiments, the filter 46 may be arranged at the inlet port 32 or anywhere within the fluid collecting space 31. Any number of sterilizing filters 46 may be installed, optionally at both the inlet port 32 and the outlet port 33.

Figure 7:
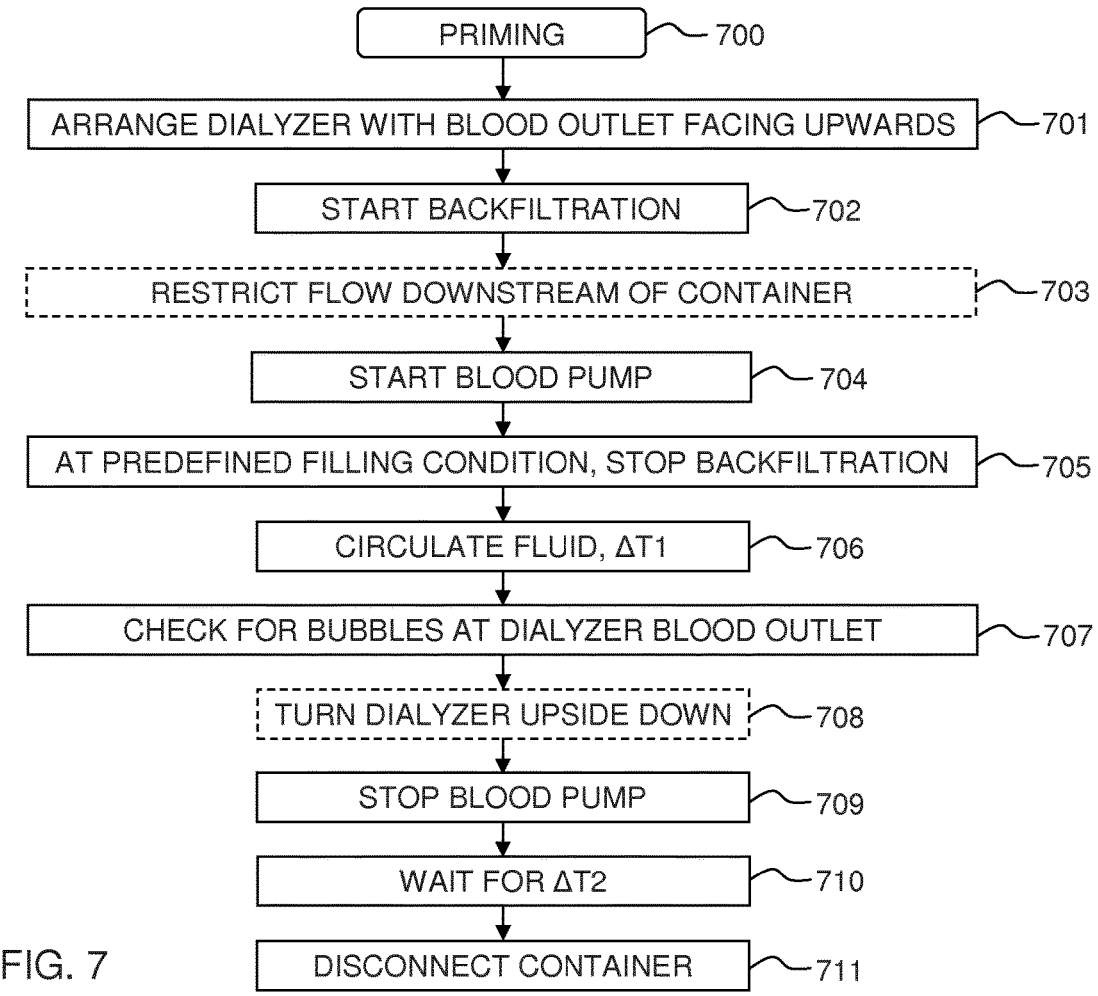
FIG. 7 is a flow chart of a method of priming a dialysis machine in accordance with a detailed example.

FIG. 7 shows a detailed example of a priming operation 700 that may be performed when the first and second flow circuits has been installed in the dialysis machine in accordance with steps 301-302 in FIG. 3. Thus, the priming operation 700 corresponds to steps 303-306 in FIG. 3 and will be given with reference to the embodiment in FIG. 4. In step 701, the dialyzer 20 is arranged with its blood outlet facing upwards. In the embodiment of FIG. 4, step 701 is included in step 302. However, in certain dialysis machines, the holder 7 is configured to arrange the dialyzer 20 with its blood outlet (i.e. connector 22) facing downwards. In such dialysis machines, step 701 will be performed by the operator, e.g. by disconnecting the dialyzer 20 from the holder 9 and turning the dialyzer upside down. In step 702, the dialysis machine 1 is operated to start backfiltration, in which priming fluid is pushed into the line arrangement 40B and the container 30. To speed up the filling of the line arrangement 40B and the container 30, it is conceivable to restrict or block the flow of priming fluid downstream of the container 30 during at least part of step 702, e.g. by the operator closing a clamp on the tubing or by the dialysis machine 1 closing the clamp 11 (step 703). When there is sufficient priming fluid in the line arrangement 40B and the container 30, any flow restriction imposed by step 703 is released and the blood pump 8 is started to circulate priming fluid in the second flow circuit C2 (step 704). At this time, the dialysis machine 1 still operates with backfiltration, causing priming fluid to flow into the second flow circuit C2. When a predefined filling condition has been achieved, the dialysis machine 1 is operated to terminate the backfiltration (step 705). The filling condition may involve attainment of a predefined level of priming fluid in the container 30 and, optionally, absence of visible bubbles at the dialyzer blood inlet (i.e. at the bottom of the dialyzer 20). Alternatively or additionally, the filling condition may be automatically detected by the control system 2 when a predefined amount of priming fluid has been transferred by backfiltration into the second circuit C2 via the dialyzer membrane 25, as measured by one or more sensors in the dialysis machine 1. For example, conventional dialysis machines 1 have flow sensors in the flow paths extending to and from the ports 5, 6. The amount of priming fluid transferred by backfiltration may be computed, by the control system 2, by accumulating the momentary difference between the flow rates of priming fluid through the ports 5, 6.

After step 705, the dialysis machine 1 operates the blood pump 8 to circulate the priming fluid for a first time period $\Delta T1$ (step 706). During $\Delta T1$, the operator may check for bubbles at the dialyzer blood outlet (i.e. at the top of the dialyzer 20) and tap on the dialyzer 20 to remove such bubbles (step 707). If the dialyzer 20 was turned upside down in step 701, the operator may also be instructed during $\Delta T1$ to arrange the dialyzer 20 with its blood outlet facing upwards, e.g. in the holder 7. After expiry of the time period $\Delta T1$, the dialysis machine 1 stops the blood pump 8 (step 709) and waits for a second time period $\Delta T2$ (step 710), to allow the first chamber 25 of the dialyzer 20 to be completely filled with priming fluid. After expiry of the time period $\Delta T2$, the priming is completed and the operator is instructed to disconnect the container 30 and the filter from the second flow circuit C2 (step 711).

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

For example, the foregoing description is equally applicable to any machine or apparatus which is configured to perform extracorporeal blood treatment by use of a dialyzer or an equivalent filtration unit, including but not limited to hemodialysis, hemofiltration, hemodiafiltration, plasmapheresis, extracorporeal blood oxygenation, extracorporeal liver support/dialysis, ultrafiltration, etc. With respect to hemofiltration and hemodiafiltration, the sterile fluid in the container 30 may be used as replacement or substitution fluid, which is introduced into the second flow circuit C2 during blood treatment. Compared to the above-described bolus injection and rinse back, the sterile fluid would have to be produced in larger quantities before the blood treatment.

The invention claimed is:

1. A control system for a blood treatment apparatus, said control system comprising:
   a memory; and
   a processor in operable communication with the memory, the processor configured to:
      instruct an operator to install a first flow circuit for conducting a fluid provided by the blood treatment apparatus through a dialyzer;
      instruct the operator to install a second flow circuit that is separated from the first flow circuit by a semi-permeable membrane of the dialyzer, the second flow circuit comprising connectors for connection to a vascular system of a subject during blood treatment, wherein the second flow circuit is configured to be disconnected from the vascular system and form a closed loop that includes a sterilizing filter;
      operate the blood treatment apparatus to pump a human-compatible fluid into the first flow circuit so that a portion of the human-compatible fluid flows through the semi-permeable membrane into the second flow circuit; and
      operate the blood treatment apparatus to circulate said portion of the human-compatible fluid in the closed loop of the second flow circuit, to thereby sterilize said portion of the human-compatible fluid by the sterilizing filter.

2. The control system of claim 1, wherein the second flow circuit is installed to further include a container, said processor being further configured to operate the blood treatment apparatus to collect a sterile fluid in the container, the sterile fluid being generated by circulating said portion of the human-compatible fluid in the closed loop.

3. The control system of claim 2, wherein said portion of the human-compatible fluid is circulated through the container.

4. The control system of claim 2, wherein the processor is configured to instruct the operator to form the closed loop by directly or indirectly connecting the connectors to an inlet port and an outlet port, respectively, on the container.

5. The control system of claim 4, wherein the second flow circuit is installed with the sterilizing filter being co-located with the outlet port so that said portion of the human-compatible fluid flows through the sterilizing filter when leaving the container via the outlet port.

6. The control system of claim 4, wherein the second flow circuit is installed with the sterilizing filter directly or indirectly connected to one of the inlet and outlet ports of the container.

7. The control system of claim 2, wherein the second flow circuit is installed with the sterilizing filter located within the container.

8. The control system of claim 4, wherein the inlet and outlet ports define an inlet opening and an outlet opening, respectively, inside the container, and wherein the processor is configured to instruct the operator to install the second flow circuit such that the container locates the inlet opening above the outlet opening.

9. The control system of claim 2, wherein the processor is further configured to:
   instruct the operator to connect the connectors to the vascular system of the subject, operate the blood treatment apparatus to perform said blood treatment,
   instruct the operator, subsequent to said blood treatment, to establish fluid communication between the container holding the sterile fluid and the second flow circuit, and operate the blood treatment apparatus to drive blood in the second flow circuit back into the vascular system of the subject while drawing at least a portion of the sterile fluid in the container into the second flow circuit.

10. The control system of claim 2, wherein the processor is further configured to:
   instruct the operator to connect the connectors to the vascular system of the subject and install the container holding the sterile fluid for fluid communication with the second flow circuit, and
   operate the blood treatment apparatus to perform said blood treatment, and to introduce a portion of the sterile fluid in the container into the second flow circuit during said blood treatment.

11. The control system of claim 1, wherein the processor is further configured to ventilate the second flow circuit to expel gaseous substances.

12. The control system of claim 1, wherein the processor is configured to circulate said portion of the human-compatible fluid in the closed loop of the second flow circuit so that said portion of the human-compatible fluid is passed at least once through the sterilizing filter.

13. The control system of claim 1, wherein the processor is further configured to, while the human-compatible fluid is pumped into the first flow circuit, cause a flow restriction in the first flow circuit downstream from the dialyzer.

14. The control system of claim 1, wherein the processor is configured to circulate said portion of the human-compatible fluid in the closed loop of the second flow circuit for a predefined time period after completion of said pumping the portion of the human-compatible fluid through the semi-permeable membrane into the second flow circuit.

15. The control system of claim 1, wherein the human-compatible fluid comprises one of a saline solution, a treatment fluid for use during said blood treatment, and water.

16. A blood treatment apparatus comprising a fluid supply unit configured to supply a human-compatible fluid to a first flow circuit when the first flow circuit is connected to the blood treatment apparatus, a pump operable to engage with a second flow circuit when the second flow circuit is connected to the blood treatment apparatus, and the control system of claim 1.

17. A method of preparing a blood treatment apparatus for blood treatment, said method comprising:

installing a first flow circuit for conducting a fluid provided by the blood treatment apparatus through a dialyzer, installing a second flow circuit that is separated from the first flow circuit by a semi-permeable membrane of the dialyzer, the second flow circuit comprising connectors for connection to a vascular system of a subject during a blood treatment, wherein the second flow circuit is configured to be disconnected from the vascular system and form a closed loop that includes a sterilizing filter, pumping, before the blood treatment and by the blood treatment apparatus, a human-compatible fluid into the first flow circuit so that a portion of the human-compatible fluid flows through the semi-permeable membrane into the second flow circuit, and circulating, before the blood treatment and by the blood treatment apparatus, said portion of the human-compatible fluid in the closed loop of the second flow circuit, to thereby sterilize said portion of the human-compatible fluid by the sterilizing filter.

18. A non-transitory, computer-readable medium storing instructions which, when executed by a processor, cause the processor to perform the method of claim 17.

* * * * *